United States Patent [19]

Augelli-Szafran et al.

[11] Patent Number: 5,652,237
[45] Date of Patent: Jul. 29, 1997

[54] 2-SUBSTITUTED-4H-3, 1-BENZOXAZIN-4-ONES AND BENZTHIAZIN-4-ONES AS INHIBITORS OF COMPLEMENT C1R PROTEASE FOR THE TREATMENT OF INFLAMMATORY PROCESSES

[75] Inventors: Corinne Elizabeth Augelli-Szafran, Ypsilanti; Bradley William Caprathe, Livonia; John Lodge Gilmore; Sheryl Jeanne Hays, both of Ann Arbor; Juan Carlos Jaen, Plymouth; Jan Ruth Penvose-Yi, Ann Arbor, all of Mich.

[73] Assignee: Warner-Lambert Company, Morris Plains, N.J.

[21] Appl. No.: 501,507

[22] Filed: Aug. 10, 1995

Related U.S. Application Data

[63] Continuation-in-part of Ser. No. 303,923, Sep. 9, 1994, abandoned.

[51] Int. Cl.[6] .................. A61K 31/54; A61K 31/535; C07C 279/08; C07D 265/12; C07D 279/16
[52] U.S. Cl. .................. 514/230.5; 514/224.2; 514/229.8; 544/50; 544/89; 544/92
[58] Field of Search .................. 544/89, 92, 50; 514/229.8, 230.5, 224.2

[56] References Cited

U.S. PATENT DOCUMENTS

| | | | |
|---|---|---|---|
| 3,450,700 | 6/1969 | Sayigh et al. | 260/244 |
| 4,002,620 | 1/1977 | Pelosi, Jr. | 260/243 R |
| 4,002,621 | 1/1977 | Pelosi, Jr. | 260/243 R |
| 4,315,766 | 2/1982 | Hamprecht et al. | 71/88 |
| 4,657,893 | 4/1987 | Krantz et al. | 514/18 |
| 4,745,116 | 5/1988 | Krantz et al. | 514/230.5 |
| 4,777,182 | 10/1988 | Fujii et al. | 514/392 |
| 4,820,730 | 4/1989 | Fujii et al. | 514/510 |

FOREIGN PATENT DOCUMENTS

| | | |
|---|---|---|
| 466944A1 | 1/1992 | European Pat. Off. . |
| 1956043 | 5/1971 | Germany . |
| 2315303 | 3/1973 | Germany . |

OTHER PUBLICATIONS

Anders et al., Chemical Abstracts 61:8321d–g, Belg. 632, 578 abstracted therein. 1964.
T. Nakayama, et al., *Chem Pharm Bull*, 1993, 41:1, 117–125.
S. Tomlinson, *Current Opin in Immunology*, 1993, 5:83–89.
A. Ohshima, et al., *Proc Natl Acad Sci USA*, 1992, 89:1016–1020.
S. Haga, et al., *Brain Research*, 1993, 601:88–94.
P. Eikelenboom, et al., *Age*, 1993, 16:2, 51–52.
J. Rogers, et al., *Neurology*, 1993, 43:1609–1611.
J.C.S. Breitner, et al., *Neurology*, 1994, 44:227–232.
T. Teshima, et al., *J Biological Chemistry*, 1982, 257:9, 5085–5091.
I. Bitter, et al. *Chemical Abstracts*, 1982, 96:1, #96:6663x.
PCT Search Report, mailed Dec. 12, 1995.

*Primary Examiner*—Peter O'Sullivan
*Attorney, Agent, or Firm*—Elizabeth M. Anderson

[57] ABSTRACT

This invention concerns certain 2-substituted-3,1-benzoxazin-4-ones and benzthiazinones as complement C1r protease inhibitors and antiinflammatory agents, pharmaceutical compositions containing them, methods of using them, and processes for their preparation.

20 Claims, No Drawings

2-SUBSTITUTED-4H-3, 1-BENZOXAZIN-4-ONES AND BENZTHIAZIN-4-ONES AS INHIBITORS OF COMPLEMENT C1R PROTEASE FOR THE TREATMENT OF INFLAMMATORY PROCESSES

This application is a continuation-in-part of U.S. application Ser. No. 08/303,923, filed Sep. 9, 1994, now abandoned.

BACKGROUND OF THE INVENTION

Serine proteases are a group of endopeptidase enzymes which have a serine amino acid in their active center. Representative serine proteases include trypsin, thrombin, and plasmin related to blood coagulation and the fibrinolysis system (*Chem. Pharm. Bull.*, 41(1):117 (1993)). Additionally, C1r and C1s in the complement system are serine proteases and provide a critical and multifaceted defense system in the host defense against infection. Constituting about 10% of the globulins in normal serum, the complement system is composed of many different proteins that are important in the immune system's response to foreign antigens. The complement system becomes activated when its primary components are cleaved and the products alone or with other proteins activate additional complement proteins resulting in a proteolytic cascade. Following activation, the complement cascade can increase vascular permeability, promote chemotaxis by phagocyte recognition, or kill microorganisms directly by lysis. Complement activation products are also involved in the adaptive immune responses that lead to antibody production (*Current Opinion in Immunology*, 5:83 (1993)).

Alzheimer's disease (AD) is the most common degenerative dementia affecting primarily the elderly population. The disease is characterized by the decline of multiple cognitive functions and a progressive loss of neurons in the central nervous system. Deposition of beta-amyloid peptide has also been associated with AD. Over the last decade, a number of investigators have noted that AD brains contain many of the classical markers of immunemediated damage. These include elevated numbers of microglia cells (these are believed to be an endogenous CNS form of the peripheral macrophage) and astrocytes. Of particular importance, complement proteins have been immunohistochemically detected in the AD brain and they most often appear associated with beta-amyloid containing pathological structures known as senile plaques (*Proc. Natl. Acad. Sci. USA*, 89:10016 (1992), *Brain Research*, 601:88 (1993), *Age*, 16(2):51 (1993)).

These initial observations which suggest the existence of an inflammatory component in the neurodegeneration observed in AD has been extended to the clinic. A small clinical study using the nonsteroidal antiinflammatory drug, indomethacin, indicated that indomethacin significantly slowed the progression of the disease (*Neurology*, 43(8):1609 (1993)). A larger study with indomethacin is presently ongoing. In addition, a study examining age of onset among 50 elderly twin pairs with onsets of AD separated by three or more years, suggested that antiinflammatory drugs may prevent or delay the initial onset of AD symptoms (*Neurology*, 44:227 (1994)).

U.S. Pat. No. 4,657,893 covers 2-amino-4H-3,1-benzoxazin-4-ones of formula

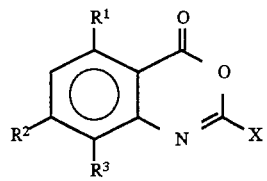

and the pharmaceutically acceptable esters and salts thereof, wherein:

$R_1$ is hydrogen or lower alkyl;

$R_2$ and $R_3$ are each independently hydrogen, halogen, lower alkyl, hydroxy, lower alkoxy, lower thioalkyl, —NO$_2$, —N(R')$_2$, —NR'COR', —NHCON(R')$_2$, or —NHCOOR', with the proviso that at least one of $R_1$, $R_2$, and $R_3$ is not hydrogen when X is NHR or NR'COR"; and X is a radical chosen from the group consisting of:

and

in which:

R is lower alkyl, lower alkenyl, lower alkynyl, optionally substituted lower cycloalkyl, or optionally substituted phenyl lower alkyl;

each R' is independently hydrogen or lower alkyl, or lower alkenyl or lower alkynyl where the unsaturated bond is at least one carbon removed from the O or N atom;

each R" is independently R, lower alkoxy, NHR', or AOR'; and

A is an amino acid residue, or a peptide of 2 to 3 amino acid residues.

The compounds are disclosed as being useful as enzyme inhibitors.

U.S. Pat. No. 4,745,116 covers 2-oxy-4H-3,1-benzoxazin-4-ones, useful as serine protease inhibitors. They are represented by formula

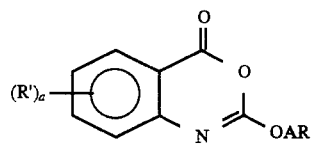

and the pharmaceutically acceptable acid additional salts thereof, wherein:

a is an integer of 1 to 4;

A is a bond, or alkylene having 1 to 8 carbon atoms;

R is hydrogen, phenyl, imidazolyl, or cycloalkyl having 3 to 6 carbon atoms, wherein the phenyl, imidazolyl, or cycloalkyl ring is optionally substituted with 1 to 3 substituents independently selected from the group consisting of lower alkyl having 1 to 4 carbon atoms, lower alkoxy having 1 to 4 carbon atoms, —N(R₁)₂, —NO2, halo, or lower alkylthio having 1 to 4 carbon atoms, and each R' is independently selected from the group consisting of hydroxy, benzyloxy, lower alkyl having 1 to 6 atoms, lower alkenyl having 2 to 6 carbon atoms, lower alkoxy having 1 to 6 carbon atoms, lower alkylthio or halo-lower alkyl having 1 to 6 carbon atoms, halo, —NO₂, —N(R₁)₂, —NR₁CO₂R₂, —NR₁COR₂, and —NR₁C(O)N(R₁)₂, in which
    each R₁ is independently hydrogen or lower alkyl having 1 to 6 carbon atoms, or together form a piperidine or a piperazine ring optionally substituted at the ring nitrogen by lower alkyl having 1 to 4 carbon atoms or —CH₂CH₂OH;
    each R₂ is independently lower alkyl having 1 to 4 carbon atoms, A is an alkylene group if R is hydrogen, or a pharmaceutically acceptable acid addition salt thereof.

German Patent Number 2,315,303 covers N-substituted 2-amino-3,1-benzoxazin-4-one preparation by cyclizing 2-ureido-benzoic acids. The compounds are represented by Formula I

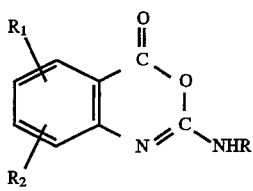

where R is alkyl or aryl optionally substituted by NO₂, halogen, alkyl, alkoxy, or aryloxy; R₁ and R₂ are H, halogen, NO₂, or optionally substituted alkyl, cycloalkyl, aralkyl, aryl, alkoxy, or aryloxy is carried out by cyclizing a compound of Formula II:

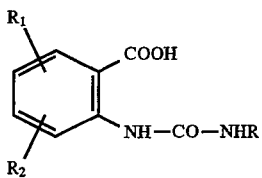

with at least an equimolar amount of a lower carboxylic anhydride dehydrating agent, optionally in the presence of an inert organic medium and/or an acid at 20°–160° C. The compounds are disclosed as intermediates for pharmaceuticals and plant protection agents.

The compounds of the instant invention are ortho-substituted where R is aryl substituted by halogen.

Those of the instant invention are unexpectedly better than those substituted at any other position. See Table I where Compound 4 is 3.5 μM and is ortho-iodo substituted. In contrast, Compounds 5 and 6, which are meta- and para-iodo substituted, are >66 μM.

U.S. Pat. No. 4,315,766 covers compounds of formula, for example,

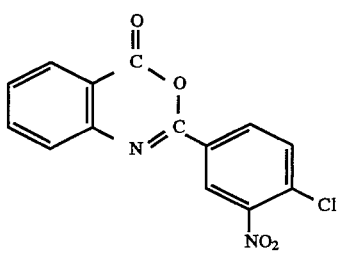

which are disclosed as useful for control of unwanted plant growth.

U.S. Pat. No. 4,777,182 and its continuation 4,820,730 cover amidine compounds of Formula I

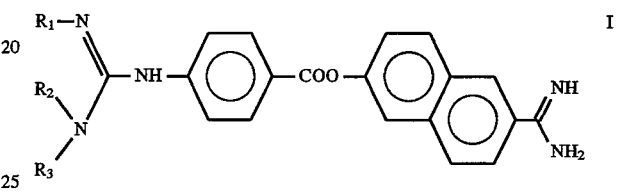

and the pharmaceutically acceptable acid addition salts thereof are novel and are of use as anti-trypsin, anti-plasmin, anti-kallikrein, anti-thrombin, and anti-complement agents which may be administered orally. These amidine compounds can be produced by the reaction between a carboxylic acid compound of Formula II

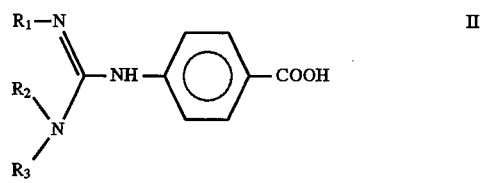

or a reactive intermediate thereof and 6-amidino-2-naphthol of Formula III

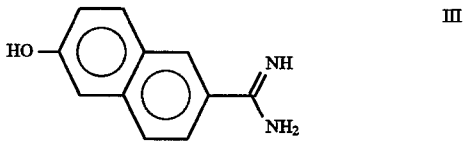

or preferably an acid addition salt thereof.

East German Patent 286,356 teaches in part the preparation of compounds of formula

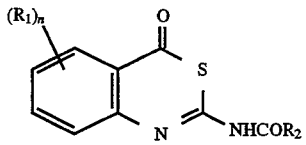

wherein R₁ is hydrogen, methyl, methoxy, or halogen and R₂ is lower alkyl (C₁–C₃), substituted or unsubstituted phenyl, chloromethyl, and alkoxy (C₁–C₂). The compounds are disclosed as biologically active and useful as intermediates.

SUMMARY OF THE INVENTION

The present invention covers compounds of formula

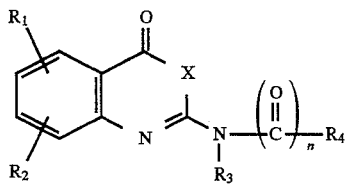

I or a pharmaceutically acceptable salt thereof wherein $R_1$ and $R_2$ are each independently hydrogen, halogen, lower alkyl, alkoxy, amino, nitro, mono-, or dialkylamino (alkyl from 1 to 6 carbon atoms), unsubstituted or alkyl-substituted guanidino or amidino (alkyl from 1 to 6 carbon atoms), or $R_1$ and $R_2$ together form a cyclopentyl, cyclohexyl, or phenyl ring fused to the ring to which they are attached;

n is an integer of from 0 to 1;

$R_3$ is hydrogen, methyl, or ethyl when n is 0; and $R_3$ is alkyl of from 1 to 8 carbons or phenyl when n is 1;

$R_4$ is phenyl mono- or disubstituted at the ortho position (s) by chlorine, bromine, iodine, or trifluoromethoxy when n is 0;

$R_4$ is phenyl, phenyl substituted by 1 to 2 groups selected from fluoro, chloro, bromo, iodo, alkyl, alkoxy, alkylthio, trifluoromethyl, unsubstituted or alkyl substituted guanidino or amidino when n=1;

$R_4$ is heteroaryl when n=1; and $R_4$ is

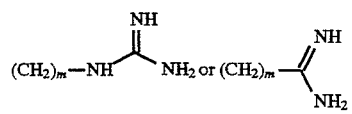

wherein m is an integer of from 2 to 6; and n is 0 or 1;
X is oxygen or sulfur.

Preferred compounds of the invention are those of Formula I wherein:

$R_1$ and $R_2$ are each independently hydrogen, halogen, alkyl of from 1 to 6 carbon atoms, nitro, trifluoromethyl, guanidino, amidino, or $R_1$ and $R_2$ together form a cyclopentyl, cyclohexyl, or phenyl ring fused to the ring to which they are attached;

n is 0;

$R_3$ is hydrogen, methyl, or ethyl;

$R_4$ is 2-chlorophenyl, 2-bromophenyl, 2-iodophenyl, 2-trifluoromethoxyphenyl, 2,6-dichlorophenyl, 2,6-diiodophenyl, unsubstituted or substituted guanidino- or amidino-phenyl,

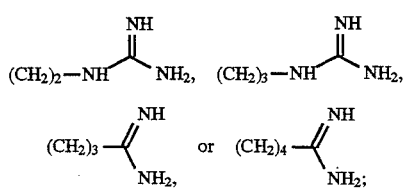

and X is oxygen or sulfur.

More preferred are compounds of Formula I wherein:

$R_1$ and $R_2$ are each independently hydrogen, 7-methyl, 6- or 7-chloro, 7-nitro or 7-trifluoromethyl, or $R_1$ and $R_2$ together form 6,7-benzo;

n is 0;

$R_3$ is hydrogen or methyl; and $R_4$ is 2-chlorophenyl, 2-bromophenyl, 2-iodophenyl, 2,6-dichlorophenyl, or 2-trifluoromethoxy.

Other preferred compounds of the invention are those of Formula I wherein:

$R_1$ and $R_2$ are each hydrogen, methyl, amidino, or guanidino;

n is 1;

$R_3$ is methyl or ethyl;

$R_4$ is phenyl, phenyl substituted by from 1 to 2 substituents selected from fluoro, chloro, bromo, iodo, alkyl, alkylthio, trifluoromethyl, amidino, guanidino, or $R_4$ is heteroaryl.

Other more preferred compounds are those of Formula I wherein:

$R_1$ and $R_2$ are each independently hydrogen, methyl, 6- or 7-amidino, or 6- or 7-guanidino;

n is 1;

$R_3$ is methyl or ethyl;

$R_4$ is phenyl, 2-iodophenyl, 2-bromophenyl, 2-thiomethylphenyl, 3-thienyl, 2-trifluoromethylphenyl, 3-amidinophenyl, 4-amidinophenyl, 3-guanidinophenyl, 4-guanidinophenyl,

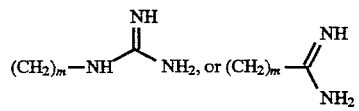

wherein m is an integer of from 2 to 5.

The most preferred compounds of the instant invention are:

2-(2-Chloro-phenylamino)-benzo[d][1,3]oxazin-4-one;

2-(2-Bromo-phenylamino)-benzo[d][1,3]oxazin-4-one;

2-(2-Iodo-phenylamino)-benzo[d][1,3]oxazin-4-one;

2-(2-Trifluoromethoxy-phenylamino)-benzo[d][1,3]oxazin-4-one;

2-(2,6-Dichloro-phenylamino)-benzo[d][1,3]oxazin-4-one;

2-[Methyl-(2-iodo-phenylamino]benzo[d][1,3]oxazin-4-one;

2-(2-Iodo-phenylamino)-naphtho[2,3-d][1,3]oxazin-4-one;

2-Iodo-N-methyl-N-(4-oxo-4H-benzo[d][1,3]oxazin-2-yl)-benzamide;

2-Bromo-N-methyl-N-(4-oxo-4H-benzo[d][1,3]oxazin-2-yl)-benzamide;

N-Methyl-2-methylsulfanyl-N-(4-oxo-4H-benzo[d][1,3]oxazin-2-yl)-benzamide;

N-Methyl-N-(4-oxo-4H-benzo[d][1,3]oxazin-2-yl)-2-trifluoromethyl-benzamide;

N-Methyl-N-(4-oxo-4H-benzo[d][1,3]oxazin-2-yl)benzamide;

2-Iodo-N-methyl-N-(6-methyl-4-oxo-4H-benzo[d][1,3]oxazin-2-yl)-benzamide;

7-Chloro-2-(2-iodo-phenylamino)-benzo[d][1,3]oxazin-4-one;

6-Chloro-2-(2-iodo-phenylamino)-benzo[d][1,3]oxazin-4-one;

2-(2-Iodo-phenylamino)-7-methyl-benzo[d][1,3]oxazin-4-one;

2-(2-Iodo-phenylamino)-7-nitro-benzo[d][1,3]oxazin-4-one;

2-(2-Iodo-phenylamino)-7-trifluoromethyl-benzo[d][1,3]-oxazin-4-one;

6,7-Dichloro-2-(2-iodo-phenylamino)-benzo[d][1,3]oxazin-4-one;

Thiophene-3-carboxylic acid methyl-(4-oxo-4H-benzo[d][1,3]oxazin-2-yl)-amide;

3-Guanidino-N-methyl-N-(4-oxo-4H-benzo[d][1,3]oxazin-2-yl)-propionamide;

4-Guanidino-N-methyl-N-(4-oxo-4H-benzo[d][1,3]oxazin-2-yl)-butyramide;

4-Carbamimidoyl-N-methyl-N-(4-oxo-4H-benzo[d][1,3]oxazin-2-yl)-butyramide;

5-Carbamimidoyl-pentanoic acid methyl-(4-oxo-4H-benzo[d][1,3]oxazin-2-yl)-amide;

N-(7-Guanidino-4-oxo-4H-benzo[d][1,3]oxazin-2-yl)-N-methyl-benzamide;

N-(7-Carbamimidoyl-4-oxo-4H-benzo[d][1,3]oxazin-2-yl)-N-methyl-benzamide;

N-(6-Guanidino-4-oxo-4H-benzo[d][1,3]oxazin-2-yl)-N-methyl-benzamide;

N-(6-Carbamimidoyl-4-oxo-4H-benzo[d][1,3]oxazin-2-yl)-N-methyl-benzamide;

4-Guanidino-N-methyl-N-(4-oxo-4H-benzo[d][1,3]oxazin-2-yl)-benzamide;

3-Guanidino-N-methyl-N-(4-oxo-4H-benzo[d][1,3]oxazin-2-yl)-benzamide;

4-Carbamimidoyl-N-methyl-N-(4-oxo-4H-benzo[d][1,3]oxazin-2-yl)-benzamide;

3-Carbamimidoyl-N-methyl-N-(4-oxo-4H-benzo[d][1,3]oxazin-2-yl)-benzamide;

N-{4-[Methyl-(4-oxo-4H-benzo[d][1,3]oxazin-2-yl)amino]-phenyl}-guanidine;

N-{3-[Methyl-(4-oxo-4H-benzo[d][1,3]oxazin-2-yl)amino]-phenyl}-guanidine;

4-[Methyl-(4-oxo-4H-benzo[d][1,3]oxazin-2-yl)amino]-benzamidine;

3-[Methyl-(4-oxo-4H-benzo[d][1,3]oxazin-2-yl)amino]-benzamidine;

Thiophene-3-carboxylic acid methyl-(4-oxo-4H-benzo[d][1,3]oxazin-2-yl)-amide;

N-(5-Chloro-4-oxo-4H-benzo[d][1,3]oxazin-2-yl)-2-iodo-N-methyl-benzamide;

2-(2-Chloro-phenylamino)-7-methyl-benzo[d][1,3]oxazin-4-one;

2-Iodo-N-methyl-N-(7-methyl-4-oxo-4H-benzo[d][1,3]oxazin-2-yl)-benzamide;

6,7-Difluoro-2-(2-iodo-phenylamino)-benzo[d][1,3]oxazin-4-one;

7-Fluoro-2-(2-iodo-phenylamino)-benzo[d][1,3]oxazin-4-one;

6,7-Dichloro-2-(2-chloro-phenylamino)-benzo[d][1,3]oxazin-4-one;

2-(2-Iodo-phenylamino)-7-trifluoromethyl-benzo[d][1,3]oxazin-4-one;

N-(6,7-Dichloro-4-oxo-4H-benzo[d][1,3]oxazin-2-yl)-2-iodo-N-methyl-benzamide;

7-Chloro-2-(2,6-dichloro-phenylamino)-benzo[d][1,3]oxazin-4-one;

2-o-Tolylamino-benzo[d][1,3]oxazin-4-one;

2-(2-Chloro-phenylamino)-7-nitro-benzo[d][1,3]oxazin-4-one;

2-(2,6-Dichloro-phenylamino)-7-trifluoromethylbenzo[d][1,3]oxazin-4-one;

Furan-2-carboxylic acid methyl-(4-oxo-4H-benzo[d][1,3]oxazin-2-yl)-amide;

Naphthalene-1-carboxylic acid methyl-(4-oxo-4H-benzo[d][1,3]oxazin-2-yl)-amide;

N-Methyl-N-(4-oxo-4H-benzo[d][1,3]oxazin-2-yl)nicotinamide;

4-Butyl-N-methyl-N-(4-oxo-4H-benzo[d][1,3]oxazin-2-yl)-benzamide;

4-Methoxy-N-methyl-N-(4-oxo-4H-benzo[d][1,3]oxazin-2-yl)-benzamide; and

4-Cyano-N-methyl-N-(4-oxo-4H-benzo[d][1,3]oxazin-2-yl)-benzamide.

The very most preferred compounds of the invention are:

2-[(2-Iodo-phenylamino]-benzo[d][1,3]oxazin-4-one;

2-(2,6-Dichloro-phenylamino)-benzo[d][1,3]oxazin-4-one;

7-Chloro-2-(2-iodo-phenylamino)-benzo[d][1,3]oxazin-4-one;

6,7-Dichloro-2-(2-iodo-phenylamino)-benzo[d][1,3]oxazin-4-one;

2-(2-Iodo-phenylamino)-7-nitro-benzo[d][1,3]oxazin-4-one;

2-(2-Iodo-phenylamino)-7-trifluoromethylbenzo[d][1,3]oxazin-4-one;

2-[Methyl-(2-iodo-phenylamino]-benzo[d][1,3]oxazin-4-one;

N-Methyl-2-iodo-N-(4-oxo-4H-benzo[d][1,3]oxazin-2-yl)-benzamide;

N-Methyl-2-trifluoromethyl-N-(4-oxo-4H-benzo[d][1,3]oxazin-2-yl)-benzamide;

N-Methyl-2-methylsulfanyl-N-(4-oxo-4H-benzo[d][1,3]oxazin-2-yl)-benzamide;

3-Guanidino-N-methyl-N-(4-oxo-4H-benzo[d][1,3]thiazin-2-yl)-propionamide;

4-Guanidino-N-methyl-N-(4-oxo-4H-benzo[d][1,3]thiazin-2-yl)-butyramide;

4-Carbamimidoyl-N-methyl-N-(4-oxo-4H-benzo[d][1,3]thiazin-2-yl)-butyramide;

5-Carbamimidoyl-pentanoic acid methyl-(4-oxo-4H-benzo[d][1,3]thiazin-2-yl)-amide;

4-Carbamimidoyl-N-methyl-N-(4-oxo-4H-benzo[d][1,3]thiazin-2-yl)-benzamide;

4-Guanidino-N-methyl-N-(4-oxo-4H-benzo[d][1,3]thiazin-2-yl)-benzamide;

3-Carbamimidoyl-N-methyl-N-(4-oxo-4H-benzo[d][1,3]thiazin-2-yl)-benzamide;

3-Guanidino-N-methyl-N-(4-oxo-4H-benzo[d][1,3]thiazin-2-yl)-benzamide;

N-(7-Guanidino-4-oxo-4H-benzo[d][1,3]oxazin-2-yl)-2-iodo-N-methyl-benzamide;

N-(7-Guanidino-4-oxo-4H-benzo[d][1,3]oxazin-2-yl)-N-methyl-2-trifluoromethyl-benzamide;

N-(7-Guanidino-4-oxo-4H-benzo[d][1,3]thiazin-2-yl)-N-methyl-benzamide;

N-(7-Carbamimidoyl-4-oxo-4H-benzo[d][1,3]thiazin-2-yl)-N-methyl-benzamide;

N-(6-Guanidino-4-oxo-4H-benzo[d][1,3]thiazin-2-yl)-N-methyl-benzamide; and

N-(6-Carbamimidoyl-4-oxo-4H-benzo[d][1,3]thiazin-2-yl)-N-methyl-benzamide.

The present invention also includes a pharmaceutical composition of compounds of Formula I for the treatment of a condition advantageously affected by the inhibition of serine proteases. The condition includes inflammatory disorders such as arthritis, rheumatoid arthritis, osteoarthritis, inflammation of autoimmune diseases, systemic lupus erythematosus (SLE), SLE nephritis, proliferative nephritis, myasthenia gravis, Crohn's disease, inflammatory bowel disease, adult respiratory syndrome, psoriasis, asthma, acute pancreatitis and uveitis. Other indications would include, but are not limited to Alzheimer's disease, ischemia-induced cell damage, particularly brain damage caused by stroke, traumatic brain injury, Guillain Barre Syndrome, Parkinson's disease, allergic encephalitis, and multiple sclerosis. Other disorders of inappropriate or undesirable complement activation include hemolysis complications, hyperacute allograft rejection, xenograft rejection, corneal graft rejection, interleukin-2 induced toxicity during IL-2 therapy and paroxysmal nocturnal hemoglobinuria. Other conditions treatable by serine protease inhibitors include blood coagulation abnormalities.

The present invention also includes methods of treating the above conditions.

The present invention also includes new uses of compounds known in U.S. Pat. No. 4,657,893. The compounds are useful in treating cognitive decline such as Alzheimer's. Compounds of formula

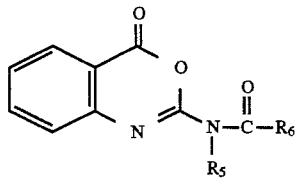

II or a pharmaceutically acceptable salt thereof wherein $R_5$ is hydrogen, methyl, ethyl, or phenyl, and $R_6$ is alkyl of from 1 to 10 carbons, alkenyl of from 2 to 6 carbons, cycloalkyl of from 3 to 6 carbons, or alkylaryl. Compounds particularly useful in the treatment are selected from Heptanoic acid methyl-(4-oxo-4H-benzo[d][1,3]oxazin-2-yl)-amide;

Cyclohexanecarboxylic acid methyl-(4-oxo-4H-benzo[d][1,3]oxazin-2-yl)-amide;

Heptanoic acid ethyl-(4-oxo-4H-benzo[d][1,3]oxazin-2-yl)-amide;

Undecanoic acid methyl-(4-oxo-4H-benzo[d][1,3]oxazin-2-yl)-amide;

N-Methyl-N-(4-oxo-4H-benzo[d][1,3]oxazin-2-yl)-3-phenyl-propionamide;

N-Methyl-N-(4-oxo-4H-benzo[d][1,3]oxazin-2-yl) acetamide;

Hexanoic acid methyl-(4-oxo-4H-benzo[d][1,3]oxazin-2-yl)-amide;

Octanoic acid methyl-(4-oxo-4H-benzo[d][1,3]oxazin-2-yl)-amide;

6-Bromo-hexanoic acid methyl-(4-oxo-4H-benzo[d][1,3]oxazin-2-yl)-amide;

N-Methyl-N-(4-oxo-4H-benzo[d][1,3]oxazin-2-yl) propionamide;

Pentanoic acid methyl-(4-oxo-4H-benzo[d][1,3]oxazin-2-yl)-amide;

Heptanoic acid (4-oxo-4H-benzo[d][1,3]oxazin-2-yl)-amide;

Heptanoic acid (4-oxo-4H-benzo[d][1,3]oxazin-2-yl)-phenyl-amide;

2-(2-Iodo-phenyl)-N-methyl-N-(4-oxo-4H-benzo[d][1,3]oxazin-2-yl)-acetamide;

Hept-3-enoic acid methyl-(4-oxo-4H-benzo[d][1,3]oxazin-2-yl)-amide; and

4-Acetylamino-N-methyl-N-(4-oxo-4H-benzo[d][1,3]oxazin-2-yl)-butyramide.

The present invention also includes using the compounds of Formula III

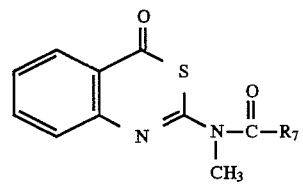

III or a pharmaceutically acceptable salt thereof wherein

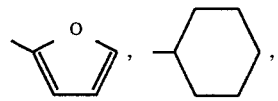

or $(CH_2)_5CH_3$ in treating a condition advantageously affected by the inhibition of serine proteases and in treating inflammation. Moreover, compounds of Formula III are novel when $R_7$ is alkyl of from 4 to 10.

DETAILED DESCRIPTION

The terms used to describe the invention are further defined below.

Halogen includes fluorine, chlorine, bromine, and iodine. Preferred are chlorine, bromine, and iodine.

Lower alkyl means a straight, branched, or cyclic hydrocarbon radical having from 1 to 8 carbon atoms unless otherwise specified and includes, for example, methyl, ethyl, n-propyl, isopropyl, sec-butyl, isobutyl, tert-butyl, and n-pentyl. The alkyl may be substituted by one or more groups selected from $R_1$ above.

The term alkoxy is O-alkyl as defined above for alkyl.

The term alkylthio is S-alkyl as defined above for alkyl.

The term heteroaryl means a heteroaromatic radical including a radical consisting of fused rings which is 2-or 3-thienyl, 2-or 3-furanyl, 2-or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4-or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, thiophenyl, pyrrolidinyl, piperidinyl, piperazinyl, morpholinyl, thiomorpholinyl, tetrahydrofuranyl, indanyl, benzofuranyl, benzothiophenyl, benzoisoxazolyl, coumarinyl, unsubstituted or substituted by 1 to 2 substituents selected from alkyl as defined above, aryl, alkoxy as defined above, thioalkoxy as defined above, hydroxy, thiol, nitro, halogen, formyl, amino, carboxyl, nitrile, —NHCOalkyl, —$CO_2H$, $CO_2$alkyl, -COalkyl, or phenyl.

The term arylalkyl means, for example, benzyl, phenethyl, and the like.

Assay of $C_1r$ Enzyme Activity

Purified human $C_1r$ was obtained commercially from Enzyme Research Labs (South Bend, Ind.). The enzyme is stored frozen at $-70°$ C. at a stock concentration of about 1 mg/mL of protein until the enzyme is needed. The enzyme can be thawed at room temperature and withstands several freeze-thaw cycles with little loss in enzyme activity. The thioester substrate, z-Gly-Arg-S-Bzl, for $C_1r$ assays (McRae, et al., 1981) is obtained commercially from Enzyme System Products (Livermore, Calif.). All other reagents were obtained from Sigma Chemical Co. (St. Louis, Mo.).

The procedure for assaying the inhibition of $C_1r$ enzyme activity is as follows. A 5 mM stock solution of z-Gly-Arg-S-Bzl is made in dimethylsulfoxide (DMSO) and stored at room temperature until needed. The stock substrate solution is diluted 3 parts stock substrate solution to 7 parts distilled water to make a 1.5 mM working substrate solution. The working substrate solution is made just before it is needed. A fresh solution of 20 µg/mL of $C_1r$ enzyme is made in 10 mM Tris buffer, pH 7.4. The enzyme solution can be stored on ice for up to an hour. A solution of 0.75 mM 5,5'-dithio-bis-2-nitrobenzoic acid (DTNB) in 150 mM Tris buffer, pH 7.5, is made fresh and can be used over several hours. Compounds at concentrations ranging from 1 mM to 0.010 mM are dissolved in DMSO and a 10 µL aliquot of each concentration is deposited in a well of a 96-well microtiter plate. Fifty microliters of the working substrate solution and 50 µL of DTNB solution are then dispensed in the wells of the microtiter plate, followed by the immediate addition of 50 µL of the $C_1r$ enzyme solution to start the assay. The assay produces a yellow color that is read in the kinetic mode using a Molecular Devices Thermomax microplate reader set to a wavelength of 405 nM. The assay background is followed by monitoring wells that contain substrate, buffer, and DTNB solutions but no enzyme. All assays are performed in triplicate at each inhibitor concentration tested. Values for each inhibitor concentration are reported as optical density (OD)/minute. The observed values are divided by control (no inhibitor) enzyme activity and multiplied by 100 to determine the percent of control activity in each assay. The concentration of inhibitor that produces 50% inhibition of enzyme activity ($IC_{50}$) is determined graphically by plotting the percent control enzyme activity against the concentration of inhibitor.

Table 1 below provides $IC_{50}$ data for the representative compounds of the invention. Many of the compounds are more potent as inhibitors of $C_1r$ than the reference agent FUT-175 ($IC_{50}$=12 µM). Example 4, which is substituted by an iodo atom in the ortho position has an $IC_{50}$ of 3.5 µM, while the para and meta iodo-substituted derivatives, Examples 5 and 6, have greatly diminished activity with $IC_{50}$s>67 µM. In all examples studied where n=0, $R_4$ required an ortho substituent for activity. The 7-Cl, the 6,7-diCl, and the 7-trifluoromethyl derivatives are extremely potent with $IC_{50}$s of 0.70, 0.50 µM, and 0.40 µM, respectively. When n=1, halogen or trifluoromethyl substitution on $R_4$ are no longer a requirement and a broader range of substituents are tolerated. For example, the thiomethyl-substituted analog has an $IC_{50}$ of 0.8 µM and the unsubstituted derivative has an $IC_{50}$ of 10.7 µM.

TABLE 1

Melting Points, Synthetic Methods, and Inhibition of C1r Inhibitors

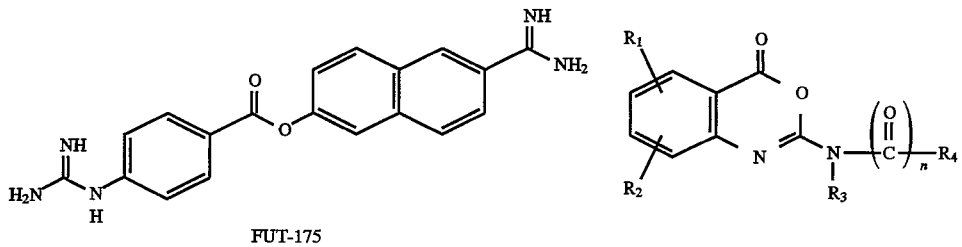

FUT-175

| Example Number | $R_1$ $R_2$ | $R_3$ | n | $R_4$ | M.P. (°C.) | Synthetic Method | Inhibition of C1r Assay 1 ($IC_{50}$, µM) |
|---|---|---|---|---|---|---|---|
| FUT-175 (reference) | | | | | | | 12 |
| 1 | H | H | 0 | o-$C_6H_4$—F | 152–155 | 1 | 50 |
| 2 | H | H | 0 | o-$C_6H_4$—Cl | 146–149 | 1 | 6.5 |
| 3 | H | H | 0 | o-$C_6H_4$—Br | 153–155 | 1 | 5.1 |
| 4 | H | H | 0 | o-$C_6H_4$—I | 140–143 | 2 | 3.5 |
| 5 | H | H | 0 | m-$C_6H_4$—I | 237–239 | 1 | >66 |
| 6 | H | H | 0 | p-$C_6H_4$—I | 190–224 | 1 | >66 |
| 7 | H | H | 0 | o,o-$C_6$—$H_3$—diCl | 261–264 | 1 | 1.3 |
| 8 | H | H | 0 | o-$C_6H_4$—SMe | 256–258 | 1 | >66 |
| 9 | H | H | 0 | o-$C_6H_4$OCF$_3$ | 168–169 | 1 | 4.0 |
| 10 | H | Me | 0 | o-$C_6H_4$—I | 104–108 | 4 | 1.4 |
| 11 | H | Et | 0 | o-$C_6H_4$—I | 129–130 | 5 | >66 |
| 12 | H | Me | 1 | o-$C_6H_4$—I | 141–143 | 3 | 3.1 |
| 13 | H | Me | 1 | o,o-$C_6H_3$—diCl | 128–132 | 3 | 8.0 |
| 14 | H | Me | 1 | o-$C_6H_4$—Br | 101–103 | 3 | 4.0 |
| 15 | H | Me | 1 | o-$C_6H_4$—SMe | 91–93 | 3 | 0.8 |
| 16 | H | Me | 1 | o-$C_6H_4$—CF$_3$ | 108–109 | 3 | 1.5 |
| 17 | H | Me | 1 | $C_6H_5$ | 99–100 | 3 | 10.7 |
| 18 | H | Et | 1 | o-$C_6H_4$—I | 82–83 | 3 | 8.3 |

TABLE 1-continued

Melting Points, Synthetic Methods, and Inhibition of C1r Inhibitors

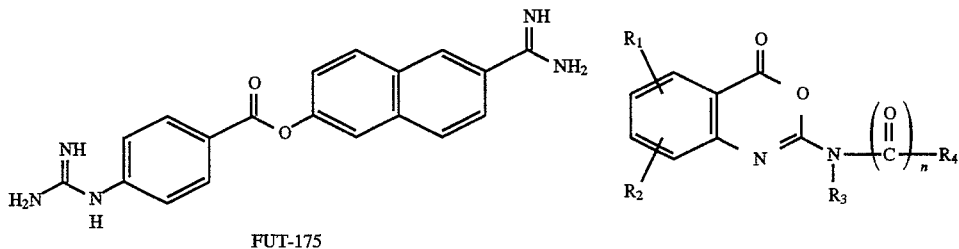

FUT-175

| Example Number | R₁ R₂ | R₃ | n | R₄ | M.P. (°C.) | Synthetic Method | Inhibition of C1r Assay 1 (IC₅₀, μM) |
|---|---|---|---|---|---|---|---|
| 19 | 7-N(Me)₂ | H | 0 | o-C₆H₄—I | 231–232 | 2 | >66 |
| 20 | 6,7-benzo fused | H | 0 | o-C₆H₄—I | 190–194 | 1 | 1.4 |
| 21 | 5-Cl | H | 0 | o-C₆H₄—I | 187–189 | 2 | 14.5 |
| 22 | 6-Cl | H | 0 | o-C₆H₄—I | 188–191 | 2 | 4 |
| 23 | 7-Cl | H | 0 | o-C₆H₄—I | 225–227 | 2 | 0.70 |
| 24 | 6-OMe | H | 0 | o-C₆H₄—I | 156–157 | 2 | 55 |
| 25 | 7-OMe | H | 0 | o-C₆H₄—I | 214–218 | 2 | >66 |
| 26 | 5-Me | H | 0 | o-C₆H₄—I | 203–204 | 2 | >66 |
| 27 | 6-Me | H | 0 | o-C₆H₄—I | 275–277 | 2 | >66 |
| 28 | 7-Me | H | 0 | o-C₆H₄—I | 174–176 | 2 | 0.8 |
| 29 | 6,7-diCl | H | 0 | o-C₆H₄—I | 179–180 | 2 | 0.50 |
| 30 | 7-NO₂ | H | 0 | o-C₆H₄—I | 237–239 | 2 | 0.75 |
| 31 | 7-CF₃ | H | 0 | o-C₆H₄—I | 177–179 | 2 | 0.40 |
| 32 | H | Me | 1 | 3-thienyl | 100–102 | 3 | 6.0 |
| 33 | H | Me | 1 | o-C₆H₄—F | 105–106 | 3 | 60 |
| 34 | H | Me | 1 | o-C₆H₄—Cl | 90–92 | 3 | 16 |
| 35 | H | Me | 1 | o-C₆H₄—OMe | 84–88 | 3 | >66 |
| 36 | H | Me | 1 | o-C₆H₄—Me | 92–93 | 3 | >67 |
| 37 | H | Me | 1 | m-C₆H₄—I | 142–143 | 3 | 20 |
| 38 | H | Me | 1 | p-C₆H₄—I | 173–175 | 3 | 33 |
| 39 | 5-Me | Me | 1 | o-C₆H₄—I | 112–115 | 3 | >66 |
| 40 | 6-Me | Me | 1 | o-C₆H₄—I | 83–84 | 3 | 1.3 |
| 41 | 6-Cl | Me | 1 | o-C₆H₄—I | 98–100 | 3 | >66 |
| 42 | 7-Cl | Me | 1 | o-C₆H₄—I | 104–105 | 3 | 18 |
| 43 | 6-OMe | Me | 1 | o-C₆H₄—I | 99–102 | 3 | 48 |
| 44 | 7-OMe | Me | 1 | o-C₆H₄—I | 108–110 | 3 | >66 |
| 45 | 7-Me | H | 0 | o-C₆H₄—Cl | 153–156 | 2 | 1.4 |
| 46 | 6,7-diF | H | 0 | o-C₆H₄—I | 173–174 | 2 | 7.0 |
| 47 | 7-F | H | 0 | o-C₆H₄—I | 186–189 | 2 | no data |
| 48 | 6,7-diCl | H | 0 | o-C₆H₄—Cl | 237–238 | 2 | 2 |
| 49 | 7-CF₃ | H | 0 | o-C₆H₄—I | 177–179 | 2 | 0.4 |
| 50 | 7-Cl | H | 0 | o,o-C₆H₃—diCl | 225–229 | 2 | 0.4 |
| 51 | H | H | 0 | o-C₆H₄—Me | 157–159 | 2 | 31 |
| 52 | 7-NO₂ | H | 0 | o-C₆H₄—Cl | 243–246 | 2 | 1.4 |
| 53 | H | H | 0 | o,o-C₆H₃—diCl | 208–211 | 2 | 1.5 |
| 54 | 5-Cl | Me | 1 | o-C₆H₄—I | 142–143 | 3 | 36 |
| 55 | 7-Me | Me | 1 | o-C₆H₄—I | 106–108 | 3 | 2.8 |
| 56 | 6,7-diCl | Me | 1 | o-C₆H₄—I | 141–145 | 3 | 8.0 |
| 57 | H | Me | 1 | 1-naphthyl | 95–100 | 3 | 23.4 |
| 58 | H | Me | 1 | p-C₆H₄—Bu | 53–56 | 3 | 16 |
| 59 | H | Me | 1 | p-C₆H₅—OMe | 142–144 | 3 | 19 |
| 60 | H | Me | 1 | p-C₆H₄—CN | 150–164 | 3 | |
| 61 | H | Me | 1 | 2-furanyl | 94–97 | 3 | 10.1 |
| 62 | H | Me | 1 | 3-pyridyl | 108–113 | 3 | 40 |
| 63 | H | Me | 1 | 3-thienyl | 100–102 | 3 | 6.0 |

Assay 2 uses the substrate ZVGR-pNA for determining inhibition of human complement protease $C_1r$ as shown in Table 2. The assay was performed in a 96-well format. Fifty microliters of water were added to each well followed by 2.5 μL of an inhibitory agent, usually in dimethyl foramide (DMF) (or water). A $C_1r$ solution (100 μL) containing 0.1 μg of activated human $C_1r$ and 100 mM Tris-HCl (pH 7.4 at 25° C.) was then added. The mixture was incubated for 10 minutes at 25° C. The reaction was then started by the addition of 100 μL of a 3 mM (Cbz-Val-Gly-Arg-p-nitroanilide) ZVGR-pNA solution. The final reaction mixture (250 μL) contained 40 mM of Tris-HCl, 1.2 mM of ZVGR-pNA, 0.1 μg $C_1R$ and certain concentration of an inhibitor. The production of p-nitroaniline was monitored at 405 nm every 15 minutes up to 90 minutes (at 25° C.). The velocity was linear for at least 60 minutes.

TABLE 2

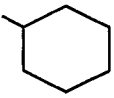

| Example Number | $R_5$ | $R_6$ | M.P. (°C.) | Inhibition of Clr Assay 1 $IC_{50}$ (μM) | ZVGRpNA - Assay 2 | Synthetic Method |
|---|---|---|---|---|---|---|
| 64 | Me | $(CH_2)_5CH_3$ | — | 0.68 | 0.0478 | 3 |
| 65 | Me | (cyclohexyl) | 93–95 | 1.2 | 0.0078 | 3 |
| 66 | Et | $(CH_2)_5CH_3$ | — | 6.32 | 0.029 | 3 |
| 67 | Me | $(CH_2)_9CH_3$ | 49–53 | >62.5 | 0.50 | 3 |
| 68 | Me | $(CH_2)_2Ph$ | 89–90 | 1.3 | 0.103 | 3 |
| 69 | Me | Me | 90–94 | 30 | 0.399 | 3 |
| 70 | Me | $(CH_2)_4CH_3$ | | | | 3 |
| 71 | Me | $(CH_2)_6CH_3$ | | | | 3 |
| 72 | Me | $CH_2CH_3$ | | | | 3 |
| 73 | Me | $(CH_2)_3CH_3$ | | | | |
| 74 | H | $(CH_2)_5CH_3$ | | | | |
| 75 | Ph | $(CH_2)_5CH_3$ | | | | |
| 76 | Me | $CH_2CH=CH(CH_2)_2CH_3$ | | | | |

Some of the compounds of Formula I are capable of further forming pharmaceutically acceptable acid addition salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzensoulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science,* 66:1–19 (1977)).

Certain of the compounds Of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term preparation is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as inhibitors of a serine protease, as agents for the treatment of inflammatory disorders caused by inappropriate or undesirable complement activation, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

Synthetic Methods

2-Amino benzoxazinones were synthesized by the general routes described in the literature (*J. Med. Chem.*, 33:464 (1990)). When $R_1$ and $R_2$ are hydrogen, commercially available 2-methoxycarbonylphenyl isocyanate was added to an appropriately substituted aniline to form the (thio)urea as shown in Method 1. Useful solvents for this reaction include, but are not limited to tetrahydrofuran, diethyl ether, benzene, toluene, acetonitrile, methylene chloride, chloroform, ethyl acetate, and dimethylformamide. The urea can then be cyclized to the targeted benzoxazinone by acid treatment using reagents such as sulphuric acid, hydrochloric acid, phosphoric acid, acetic acid, or methanesulphonic acid.

METHOD 1

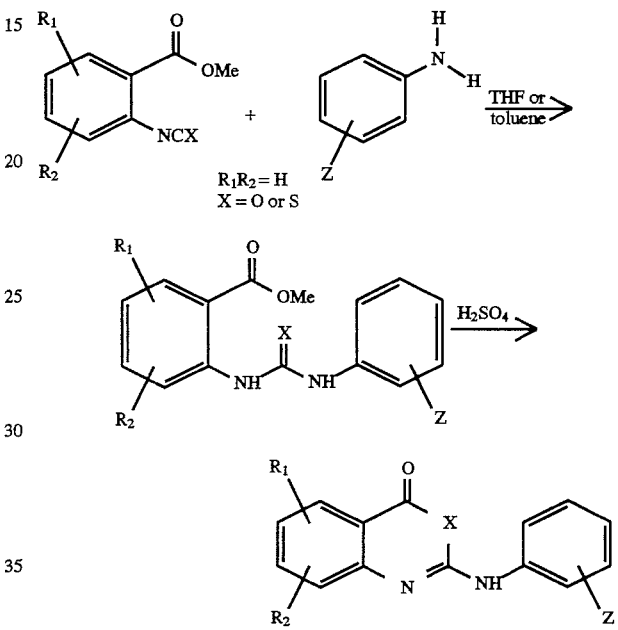

When $R_1$ and $R_2$ do not equal hydrogen, the appropriately substituted anthranilic acid was synthesized and treated with a substituted isocyanate or thioisocyanate to afford the (thio)urea as shown in Method 2. The (thio)urea was treated in acidic media as described above to produce the benzoxazinone or benzthiazinone.

METHOD 2

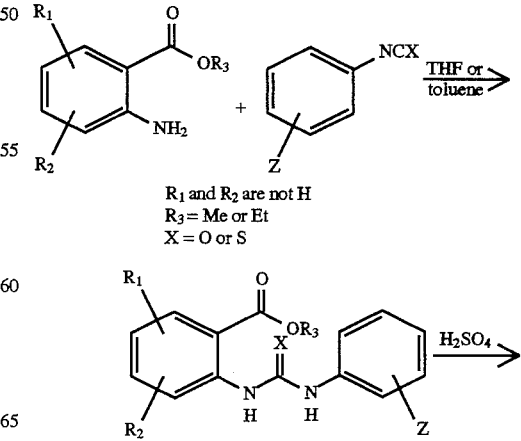

-continued
METHOD 2

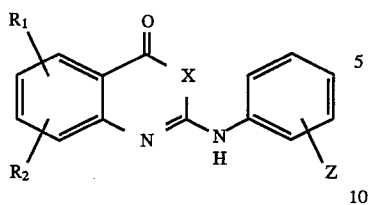

The N-acylated derivatives of the benzoxazinones or benzthiazinones were synthesized by treatment of the appropriately substituted methyl anthranilates with methyl- or ethyl-isocyanate or thioisocyanate in pyridine or another suitable solvent to form the alkyl (thio)urea. The (thio)urea was cyclized with concentrated sulfuric acid to afford the N-alkylated benzoxazinone or benzthiazinone which was subsequently acylated with an appropriately substituted acid chloride to obtain the desired product as shown in Method 3. Alternatively, the carboxyl group can be activated for acylation by means other than conversion to the acid chloride. These alternatives include activation of the carboxylic acid by treatment with such agents as an organic anhydride, dicyclohexylcarbodiimide, or carbonyl dimidazole.

METHOD 3

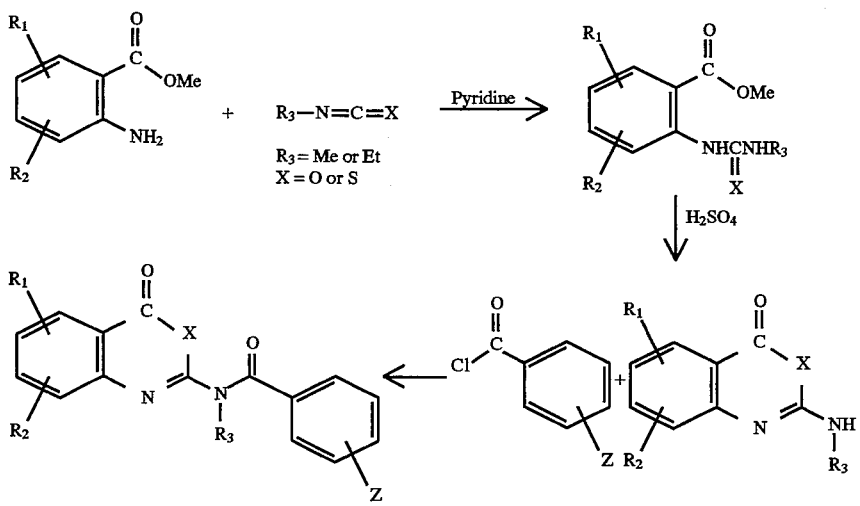

To form the N-alkylated 2-arylamino derivatives when the alkyl group is methyl or ethyl, the requisite urea or (thio) urea is formed by addition of the N-substituted aniline to the isocyanate or thioisocyanate in a solvent such as toluene or tetrahydrofuran. The benzoxazinone or benzthiazinone ring structure is subsequently formed by hydrolysis of the ester functionality followed by treatment of the acid with a coupling reagent such as benzoyl chloride, dicyclohexylcarbodiimide or 1-(3-dimethylamino-propyl)-3-ethyl-carbodiimide as shown in Method 4.

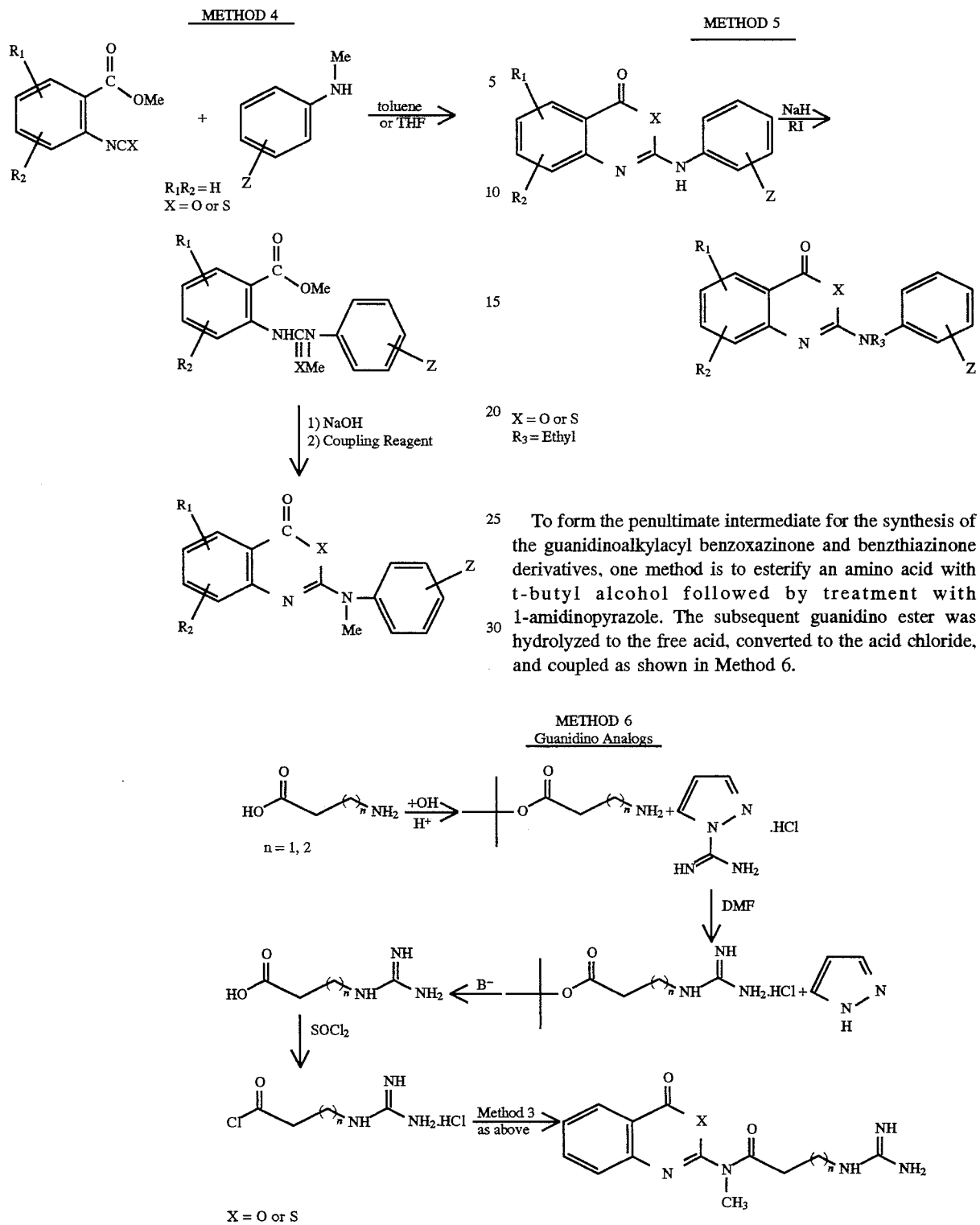

To form the penultimate intermediate for the synthesis of the guanidinoalkylacyl benzoxazinone and benzthiazinone derivatives, one method is to esterify an amino acid with t-butyl alcohol followed by treatment with 1-amidinopyrazole. The subsequent guanidino ester was hydrolyzed to the free acid, converted to the acid chloride, and coupled as shown in Method 6.

To form the N-alkylated 2-arylamino derivatives when the alkyl group is larger than methyl, it is necessary to preform the 2-arylamino benzoxazinone or 2-arylamino benzthiazinone ring structure. The desired product is then obtained by treatment with a nonnucleophilic base such as sodium hydride followed by reaction with a suitably electrophilic alkylating reagent such as an alkyl iodide or alkyl triflate as shown in Method 5.

To form the penultimate intermediate for the synthesis of the amidinoalkylacyl benzoxazinone derivatives, a cyano acid was esterified with t-butyl alcohol and treated with ammonium thiocyanate. The resulting amidino t-butyl ester was hydrolyzed to the free acid, converted to the acid chloride, and coupled as shown in Method 7.

METHOD 7
Amidino Analogs

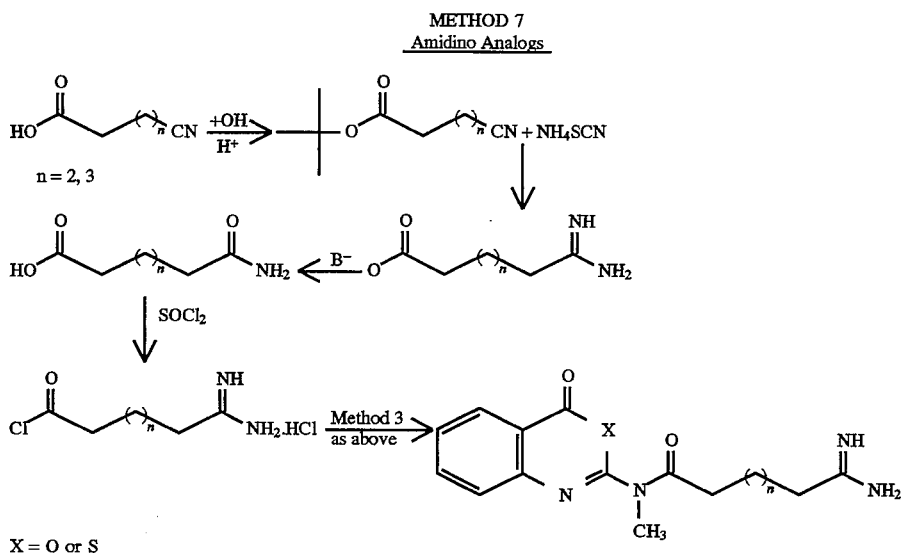

X = O or S

METHOD 1: The example numbers refer to the compounds in the tables.

EXAMPLE 1

2-(2-Fluoro-phenylamino]-benzo[d][1,3]oxazin-4-one

Step 1. 2-[3-(2-Fluoro-phenyl)-ureido]-benzoic acid methyl ester

A solution of 2-methoxycarbonylphenyl isocyanate (1.5 g, 8.5 mmol) and 2-fluoroaniline (0.9 mL, 9.3 mmol) in THF (50 mL) was stirred at room temperature for 24 hours. The solution was concentrated, dissolved in EtOAc, washed with 10% HCl and brine, dried (MgSO₄), filtered, and concentrated. Chromatography (silica gel, 20% EtOAc in hexanes) yielded the urea as a white solid, mp 178°–179° C.

Step 2. 2-(2-Fluoro-phenylamino]-benzo[d][1,3]oxazin-4-one

The urea was dissolved in concentrated sulfuric acid (5 mL) and stirred at room temperature for 1 hour. The solution was cooled and poured into a vigorously stirring mixture of EtOAc and saturated NaHCO₃ solution. The EtOAc extract was washed with brine, dried (MgSO₄), filtered, and concentrated to give the titled compound as an off-white solid, mp 152°–155° C.

Also made by above procedures were Compounds 2,3, 5,6, 8, 9, 20, and 7 as shown in Table 1.

2) 2-(2-Chloro-phenylamino)-benzo[d][1,3]oxazin-4-one;
3) 2-(2-Bromo-phenylamino)-benzo[d][1,3]oxazin-4-one;
5) 2-(3-Iodo-phenylamino)-benzo[d][1,3]oxazin-4-one;
6) 2-(4-Iodo-phenylamino)-benzo[d][1,3]oxazin-4-one;
8) 2-(2-Methylsulfanyl-phenylamino)-benzo[d][1,3]oxazin-4-one;
9) 2-(2-Trifluoromethoxy-phenylamino)-benzo[d][1,3] oxazin-4-one;
20) 2-(2-Iodo-phenylamino)-naphtho[2,3-d][1,3]oxazin-4-one; and
7) 2-(2,6-Dichloro-phenylamino-benzo[d][1,3]oxazin-4-one.

METHOD 2:

EXAMPLE 4

2-(2-Iodo-phenylamino]-benzo[d][1,3]oxazin-4-one

Step 1. 2-[3-(2-Iodo-phenyl)-ureido]-benzoic acid methyl ester

To a solution of 2-iodophenyl isocyanate (3.36 g, 13.7 mmol) in THF (250 mL) was added ethyl 2-aminobenzoate (5.1 mL, 34.5 mmol). The resulting mixture was stirred at room temperature for 8 hours, evaporated and chromatographed (silica gel, 10% EtOAc in hexanes) to give 4.4 g (78%) of ethyl 2-(2-iodophenylureido)benzoate as a white solid, mp 162°–164° C.

Step 2. 2-(2-Iodo-phenylamino]-benzo[d][1,3]oxazin-4-one

The urea was dissolved in 5 mL of concentrated sulfuric acid and stirred at 50° C. for 1 hour. The solution was cooled and poured into a vigorously stirring mixture of EtOAc and saturated NaHCO₃ solution. The EtOAc extract was washed with brine, dried (MgSO₄), filtered and concentrated to give the titled compound as a off-white solid, mp 140°–143° C.

EXAMPLE 19

7-Dimethylamino-2-(2-iodo-phenylamino)-benzo[d][1,3]oxazin-4-one

Step 1. 2-[Bis[(1,1-dimethylethoxy) carbonyl]amino]-4-nitro-benzoic acid ethyl ester Ethyl 4-nitroanthranilate (12.86 g, 0.061 mol) and 4-dimethylaminopyridine (9.28 g, 0.076 mol) were dissolved in anhydrous tetrahydrofuran and di-tert-butyl-dicarbonate (33.28 g, 0.152 g) was added in one portion. The reaction was stirred for 24 hours under a nitrogen atmosphere at 25° C. The reaction was concentrated under reduced pressure and the black residue was dissolved in a minimum quantity of ethyl acetate and poured onto a silica gel plug eluted initially with hexane followed by increasing quantities of ethyl acetate up to 20%. The partially purified compound was recrystallized from ethyl acetate/hexane to produce the di-boc protected aniline as a pale yellow solid, mp 109°–113° C.

Step 2. 4-Amino-2-[bis[(1,1-dimethylethoxy) carbonyl]-amino]-benzoic acid ethyl ester 2-[Bis[(1,1-dimethylethoxy)carbonyl]amino]-4-nitro-benzoic acid ethyl ester (8.35 g, 0.02 mol) was dissolved in ethanol (100 mL) and Raney nickel (2 g) was added. The mixture was hydrogenated for 18 hours, filtered and concentrated to produce the aniline as a white solid, mp 202°–204° C., dec.

Step 3. 2-[Bis [(1,1-dimethylethoxy)carbonyl]amino]-4-(dimethylamino)-benzoic acid ethyl ester 4-Amino-2-[bis[(1,1-dimethylethoxy)carbonyl]amino]-benzoic acid ethyl ester (7.70 g, 0.02 mol) was dissolved in ethanol (200 mL) and aqueous formaldehyde (50 mL). Twenty percent palladium on carbon (1.8 g) was added and the reaction was hydrogenated for 2.5 hours. The reaction was filtered and concentrated to afford a white solid which was recrystallized from methylene chloride/ethyl acetate to produce a white solid, mp 162°–164° C.

Step 4. 2-Amino-4-dimethylamino-benzoic acid ethyl ester

2-[Bis[(1,1-dimethylethoxy) carbonyl]amino]-4-(dimethylamino)-benzoic acid ethyl ester (5.57 g, 0.0136 mol) was dissolved in chloroform (80 mL) and treated with trifluoroacetic acid (10.5 mL, 0.0136 mol). The reaction was stirred at 25° C. until gas evolution ceased and then was heated to reflux for 1.7 hours. The reaction was extracted with 5% sodium bicarbonate solution and the chloroform layer was dried (MgSO$_4$), filtered, and concentrated to produce a crude residue which was chromatographed on a silica gel column eluted with petroleum ether:ethyl acetate (4:1) to produce the product as a white solid, mp 104°–106° C.

Step 5. 1-Iodo-2-isocyanato-benzene

To a stirring room temperature suspension of 2-iodoaniline hydrochloride (prepared from 5.7 g, 26.0 mmol of 1-iodoaniline and 33 mL of 1M HCl in ether solution) in toluene (500 mL) was added dropwise 12.5% phosgene (26 mL) in toluene solution. The mixture was refluxed for 1 hour, cooled, treated with additional phosgene (26 mL), and refluxed for 12 hours. The cloudy solution was concentrated, suspended into hexanes (250 mL), and filtered through a pad of Celite. The filtrate was concentrated and distilled (bp 50°–60° C., 0.5–0.25 mm) to give 5.0 g (78%) of the titled compound as a colorless liquid.

Step 6. 4-Dimethylamino-2-[3-(2-iodo-phenyl)-ureido] benzoic acid ethyl ester

2-Amino-4-dimethylamino-benzoic acid ethyl ester (1.0 g, 0.0048 mol) was dissolved in toluene (40 mL) and the 1-iodo-2-isocyanato-benzene (1.18 g, 0.0048 mol) was added dropwise over a 10 minute period. The reaction was stirred for 18 hours, and the reaction was filtered to produce the urea as a white solid.

Step 7. 7-Dimethylamino-2-(2-iodo-phenylamino)benzo [d][1,3]oxazin-4-one

4-Dimethylamino-2-[3-(2-iodo-phenyl)-ureido]benzoic acid ethyl ester (1.5 g, 0.0033 mol) was dissolved in concentrated sulfuric acid (3 mL) and stirred for 18 hours. The reaction was poured into saturated sodium bicarbonate solution, and the solid was filtered. The solid was recrystallized from methylene chloride/ethyl acetate to afford the product as a white amorphous solid, mp 231°–232° C.).

Also made by the above procedure were Compounds 21, 22, 23, 24, 25, 26, 27, 28, 29, 30, 31, 45, 46, 47, 48, 49, 50, 51, 52, and 53 as shown in Table 1.

21) 5-Chloro-2-(2-iodo-phenylamino)-benzo[d][1,3]oxazin-4-one;
22) 6-Chloro-2-(2-iodo-phenylamino)-benzo[d][1,3]oxazin-4-one;
23) 7-Chloro-2-(2-iodo-phenylamino)-benzo[d][1,3]oxazin-4-one;
24) 2-(2-Iodo-phenylamino)-7-methoxy-benzo[d][1,3] oxazin-4-one;
25) 2-(2-Iodo-phenylamino)-5-methyl-benzo[d][1,3]oxazin-4-one;
26) 2-(2-Iodo-phenylamino)-6-methyl-benzo[d][1,3]oxazin-4-one;
27) 2-(2-Iodo-phenylamino)-7-methyl-benzo[d][1,3]oxazin-4-one;
28) 6,7-Dichloro-2-(2-iodo-phenylamino)-benzo[d][1,3] oxazin-4-one;
29) 2-(2-Iodo-phenylamino)-6-methoxy-benzo[d][1,3] oxazin-4-one;
30) 2-(2-Iodo-phenylamino)-7-nitro-benzo[d][1,3]oxazin-4-one;
31) 2-(2-Iodo-phenylamino)-7-trifluoromethylbenzo[d][1,3] oxazin-4-one;
45) 2-(2-Chloro-phenylamino)-7-methyl-benzo[d][1,3] oxazin-4-one;
46) 6,7-Difluoro-2-(2-iodo-phenylamino)-benzo[d][1,3] oxazin-4-one;
47) 7-Fluoro-2-(2-iodo-phenylamino)-benzo[d][1,3]oxazin-4-one;
48) 6,7-Dichloro-2-(2-chloro-phenylamino)-benzo[d][1,3] oxazin-4-one;
49) 2-(2-Iodo-phenylamino)-7-trifluoromethyl-benzo[d][1, 3]oxazin-4-one;
50) 7-Chloro-2-(2,6-dichloro-phenylamino)-benzo[d][1,3] oxazin-4-one;
51) 2-o-Tolylamino-benzo[d][1,3]oxazin-4-one;
52) 2-(2-Chloro-phenylamino)-7-nitro-benzo[d][1,3] oxazin-4-one; and
53) 2-(2,6-Dichloro-phenylamino)-benzo[d][1,3]oxazin-4-one.

METHOD 3:

EXAMPLE 15

N-Methyl-2-methylsulfanyl-N-(4-oxo-4H-benzo[d][1,3] oxazin-2-yl)-benzamide

Step 1. 2-[3-Methyl-ureido]-benzoic acid methyl ester

Methyl anthranilate (15.2 g, 0.100 mol) and methyl isocyanate (8.86 g, 0.150 mol) were combined in pyridine (50 mL) and stirred for 3 hours. During this time, a white ppt. formed. The ppt. was filtered and washed with petroleum ether (3×50 mL). The product was dried in vacuo to afford the target compound as a white solid, mp 120°–121° C.

Step 2. 2-Methylamino-benzo[d][1,3]oxazin-4-one

2-[3-Methyl-ureido]-benzoic acid methyl ester (18.0 g, 0.0856 mol) was stirred in H$_2$SO$_4$ (20 mL) for 4 hours. The reaction mixture was partitioned between 1M sodium hydroxide solution (1000 mL) and ethyl acetate (800 mL). The ethyl acetate layer was dried (MgSO$_4$), filtered, and concentrated in vacuo. The product was recrystallized from ethyl acetate to produce the target compound as a white solid, mp 202°–203° C.

Step 3. 2-Methylthiobenzoyl chloride

2-Methylthiobenzoic acid (0.202 g, 0.0012 mol) and thionyl chloride (0.238 g, 0.0020 mol) were combined in THF (20 mL) and refluxed for 2 hours. The reaction mixture was concentrated in vacuo, and the crude product was used in the next reaction without further purification.

Step 4. N-Methyl-2-methylsulfanyl-N-(4-oxo-4H-benzo [d][1,3]oxazin-2-yl)-benzamide 2-Methylthiobenzoyl chloride (0.224 g, 0.0012 mol), 2-methylamino-benzo[d][1,3]oxazin-4-one (0.200 g, 0.00114 mol), and 4-dimethylaminopyridine (10 mg) were dissolved in pyridine (10 mL), and the reaction was stirred 18 hours at 25° C. under a nitrogen atmosphere. The reaction mixture was partitioned between 5% HCl (200 mL) and methylene chloride (200 mL). The methylene chloride layer was dried (MgSO$_4$), filtered, and concentrated in vacuo. The crude residue was chromatographed on a silica gel column eluting with methylene chloride. The product was then recrystallized from ether/hexanes to produce the target compound as a white solid, mp 91°–93° C.

Also made by the above procedure were Compounds 12, 13, 14, 16, 17, 18, 32, 33, 34, 35, 36, 37, 38, 39, 40, 41, 42, 43, 44, 54, 55, 56, 57, 58, 59, 60, 61, 62, and 63 as shown in Table 1. Also, Examples 64–76 as shown in Table 2.

12) 2-Iodo-N-methyl-N-(4-oxo-4H-benzo[d][1,3]oxazin-2-yl)-benzamide;
13) 2,6-Dichloro-N-methyl-N-(4-oxo-4H-benzo[d][1,3]oxazin-2-yl)-benzamide;
14) 2-Bromo-N-methyl-N-(4-oxo-4H-benzo[d][1,3]oxazin-2-yl)-benzamide;
16) N-Methyl-N-(4-oxo-4H-benzo[d][1,3]oxazin-2-yl)-2-trifluoromethyl-benzamide;
17) N-Methyl-N-(4-oxo-4H-benzo[d][1,3]oxazin-2-yl) benzamide;
18) N-Ethyl-2-iodo-N-(4-oxo-4H-benzo[d][1,3]oxazin-2-yl)-benzamide;
32) Thiophene-3-carboxylic acid methyl-(4-oxo-4H-benzo[d][1,3]oxazin-2-yl)-amide;
33) 2-Fluoro-N-methyl-N-(4-oxo-4H-benzo[d][1,3]oxazin-2-yl)-benzamide;
34) 2-Chloro-N-methyl-N-(4-oxo-4H-benzo[d][1,3]oxazin-2-yl)-benzamide;
35) 2-Methoxy-N-methyl-N-(4-oxo-4H-benzo[d][1,3]oxazin-2-yl)-benzamide;
36) 2,N-Dimethyl-N-(4-oxo-4H-benzo[d][1,3]oxazin-2-yl)-benzamide;
37) 3-Iodo-N-methyl-N-(4-oxo-4H-benzo[d][1,3]oxazin-2-yl)-benzamide;
38) 4-Iodo-N-methyl-N-(4-oxo-4H-benzo[d][1,3]oxazin-2-yl)-benzamide;
39) 2-Iodo-N-methyl-N-(5-methyl-4-oxo-4H-benzo[d][1,3]oxazin-2-yl)-benzamide;
40) 2-Iodo-N-methyl-N-(6-methyl-4-oxo-4H-benzo[d][1,3]oxazin-2-yl)-benzamide;
41) N-(6-Chloro-4-oxo-4H-benzo[d][1,3]oxazin-2-yl)-2-iodo-N-methyl-benzamide;
42) N-(7-Chloro-4-oxo-4H-benzo[d][1,3]oxazin-2-yl)-2-iodo-N-methyl-benzamide;
43) 2-Iodo-N-(6-methoxy-4-oxo-4H-benzo[d][1,3]oxazin-2-yl)-N-methyl-benzamide;
44) 2-Iodo-N-(7-methoxy-4-oxo-4H-benzo[d][1,3]oxazin-2-yl)-N-methyl-benzamide;
54) N-(5-Chloro-4-oxo-4H-benzo[d][1,3]oxazin-2-yl)-2-iodo-N-methyl-benzamide;
55) 2-Iodo-N-methyl-N-(7-methyl-4-oxo-4H-benzo[d][1,3]oxazin-2-yl)-benzamide;
56) N-(6,7-Dichloro-4-oxo-4H-benzo[d][1,3]oxazin-2-yl)-2-iodo-N-methyl-benzamide;
57) Naphthylene-1-carboxylic acid methyl-(4-oxo-4H-benzo[d][1,3]oxazin-2-yl-amide;
58) 4-Butyl-N-methyl-N-(4-oxo-4H-benzo[d][1,3]oxazin-2-yl)-benzamide;
59) 4-Methoxy-N-methyl-N-(4-oxo-4H-benzo[d][1,3]oxazin-2-yl)-benzamide;
60) 4-Cyano-N-methyl-N-(4-oxo-4H-benzo[d][1,3]oxazin-2-yl)-benzamide;
61) Furan-2-carboxylic acid methyl-(4-oxo-4H-benzo[d][1,3]oxazin-2-yl)-amide;
62) N-Methyl-N-(4-oxo-4H-benzo[d][1,3]oxazin-2-yl) nicotinamide;
63) Thiophene-3-carboxylic acid methyl-(4-oxo-4H-benzo[d][1,3]oxazin-2-yl)-amide;
64) Heptanoic acid methyl-(4-oxo-4H-benzo[d][1,3]oxazin-2-yl)-amide;
65) Cyclohexanecarboxylic acid methyl-(4-oxo-4H-benzo[d][1,3]oxazin-2-yl)-amide;
66) Heptanoic acid ethyl-(4-oxo-4H-benzo[d][1,3]oxazin-2-yl)-amide;
67) Undecanoic acid methyl-(4-oxo-4H-benzo[d][1,3]oxazin-2-yl)-amide;
68) N-Methyl-N-(4-oxo-4H-benzo[d][1,3]oxazin-2-yl)-3-phenyl-propionamide;
69) N-Methyl-N-(4-oxo-4H-benzo[d][1,3]oxazin-2-yl) acteamide;
70) Hexanoic acid methyl-(4-oxo-4H-benzo[d][1,3]oxazin-2-yl)-amide;
71) Octanoic acid methyl-(4-oxo-4H-benzo[d][1,3]oxazin-2-yl)-amide;
72) N-Methyl-N-(4-oxo-4H-benzo[d][1,3]oxazin-2-yl) propionamide;
73) Pentanoic acid methyl-(4-oxo-4H-benzo[d][1,3]oxazin-2-yl)-amide;
74) Heptanoic acid (4-oxo-4H-benzo[d][1,3]oxazin-2-yl)-amide;
75) Heptanoic acid (4-oxo-4H-benzo[d][1,3]oxazin-2-yl)-phenyl-amide; and
76) Hept-3-enoic acid methyl-(4-oxo-4H-benzo[d][1,3]oxazin-2-yl)-amide.

METHOD 4:

EXAMPLE 10

2-[Methyl-(2-iodo-phenyl)-amino]benzo[d][1,3]oxazin-4-one

Step 1. N-Methyl-2-iodoaniline

A solution of 2-iodoaniline (6.0 g, 27.4 mmol) and ethyl formate (11.1 mL, 137.4 mmol) in 200 mL of THF was added dropwise to a suspension of sodium hydride (1.4 g, 34.2 mmol) in 250 mL of THF. The mixture was stirred at room temperature for 24 hours, quenched with water and extracted into ethyl acetate. The organic extract was dried (MgSO$_4$), filtered and concentrated to give 6.3 g of crude N-formyl-2-iodoaniline as a tan solid.

To a stirring suspension at 0° C. of sodium borohydride (3.6 g) and the above crude N-formyl-2-iodoaniline (6.3 g) in 500 mL of THF was added dropwise a solution of boron trifluoride diethyl etherate (15.7 mL) in 100 mL of THF. The mixture was allowed to warm to room temperature overnight, then recooled to 0° C. and carefully quenched with dropwise addition of water (125 mL). The mixture was basified with ammonium hydroxide and extracted into ethyl acetate. The organic extract was washed with brine, dried (MgSO$_4$), filtered, concentrated and chromatographed (silica gel, 10% ethyl acetate in hexanes) to give the title compound as tan oil. The hydrochloride salt was made and crashed out of diethyl ether to give N-methyl-2-iodoaniline, hydrochloride as a white solid, mp 154°–155° C., dec.

Step 2. 2-[N-Methyl-3-(2-iodophenyl)-ureido]-benzoic acid methyl ester

A solution of 2-methoxycarbonylphenyl isocyanate (1.0 g, 5.6 mmol), N-methyl-2-iodoaniline, hydrochloride (1.6 g, 5.9 mmol) and N,N-diisopropylethylamine (1.1 mL, 6.3 mmol) in 100 mL of toluene was refluxed under N$_2$ for 72 hours. The sample was concentrated, and partitioned between chloroform and 10% HCl. The chloroform was dried (MgSO$_4$), filtered, concentrated and chromatographed (silica gel, methylene chloride) to give the title compound as a yellow solid, mp 144°–148° C.

Step 3. 2-[Methyl-(2-iodo-phenyl)-amino]benzo[d][1,3] oxazin-4-one

A mixture of 2-[N-methyl-3-(2-iodophenyl)-ureido] benzoic acid methyl ester (0.5 g, 1.2 mmol) and 0.1N NaOH solution (17 mL, 1.7 mmol) in 20 mL of ethanol was gently refluxed for 30 minutes. The solution was cooled, concentrated, acidified with 10% HCl and extracted into ethyl acetate. The ethyl acetate extract was dried (MgSO$_4$), filtered and concentrated to give the carboxylic acid as a yellow-white solid.

This material was dissolved into 150 mL of chloroform (ethanol free) and treated with 1-(3-dimethylaminopropyl)-3-ethylcarbodiimide hydrochloride (0.3 g, 1.6 mmol). The solution was stirred at room temperature for 2 hours, washed with water, dried (MgSO$_4$), filtered, concentrated and crystallized from diethyl ether-hexanes to give the title compound as light yellow solid, mp 104°–105° C., dec.

METHOD 5:

EXAMPLE 18

2-[Ethyl-(2-iodo-phenyl)-amino]-benzo[d][1,3]oxazin-4-one 2-(2-Iodo-phenyl)-amino]-benzo[d][1,3]oxazin-4-one (0.308 g, 0.00085 mol) was dissolved in THF (5 mL), and NaH (0.040 g, 0.0010 mol) was added. The reaction was stirred for 30 minutes and ethyl iodide (0.312 g, 0.0020 mol) was added. The reaction was heated to 60° C. and stirred for 24 hours under a nitrogen atmosphere. The reaction mixture was partitioned between H$_2$O (200 mL) and ethyl acetate (200 mL). The ethyl acetate layer was dried (MgSO$_4$), filtered, and concentrated in vacuo. The crude residue was chromatographed on a silica gel column eluted with petroleum ether:ethyl acetate (7:3). The product was recrystallized from ether/hexanes to produce the target compound as a white solid, mp 129°–130° C.).

METHOD 6:

3-Guanidino-N-methyl-N-(4-oxo-4H-benzo[d][1,3] oxazin-2-yl)-propionamide
and
4-Guanidino-N-methyl-N-(4-oxo-4H-benzo[d][1,3] oxazin-2-yl)-butyramide

METHOD 7:

4-Carbamimidoyl-N-methyl-N-(4-oxo-4H-benzo[d][1,3] oxazin-2-yl)-butyramide
and
5-Carbamimidoyl-pentanoic acid methyl-(4-oxo-4H-benzo[d][1,3]oxazin-2-yl)-amide

We claim:
1. A compound of formula or a pharmaceutically acceptable salt thereof wherein
$R_1$ and $R_2$ are each independently hydrogen, halogen, lower alkyl, alkoxy, amino, nitro, mono-, or dialkylamino (alkyl from 1 to 6 carbon atoms), unsubstituted or alkyl-substituted guanidino or amidino (alkyl from 1 to 6 carbon atoms), or $R_1$ and $R_2$ together form a cyclopentyl, cyclohexyl, or phenyl ring fused to the ring to which they are attached;
n is an integer of from 0 to 1;
$R_3$ is hydrogen, methyl, or ethyl when n is 0; and
$R_3$ is alkyl of from 1 to 8 carbons or phenyl when n is 1;
$R_4$ is phenyl mono- or disubstituted at the ortho position (s) by chlorine, bromine, iodine, or trifluoromethoxy when n is 0;
$R_4$ is phenyl, phenyl substituted by 1 to 2 groups selected from fluoro, chloro, bromo, iodo, alkyl, alkoxy, alkylthio, trifluoromethyl, unsubstituted or alkyl substituted guanidino or amidino when n is 1;
$R_4$ is heteroaryl when n is 1; and
$R_4$ is $$(CH_2)_m-NH \overset{NH}{\underset{}{\|}} NH_2 \text{ or } (CH_2)_m-\overset{NH}{\underset{NH_2}{\|}}$$

wherein m is an integer of from 2 to 6; and n is 0 or 1;
X is oxygen or sulfur.

2. A compound according to claim 1 wherein
$R_1$ and $R_2$ are each independently hydrogen, halogen, alkyl of from 1 to 6 carbon atoms, nitro, trifluoromethyl, guanidino, amidino, or $R_1$ and $R_2$ together form a cyclopentyl, cyclohexyl, or phenyl ring fused to the ring to which they are attached;
n is 0;
$R_3$ is hydrogen, methyl, or ethyl;
$R_4$ is 2-chlorophenyl, 2-bromophenyl, 2-iodophenyl, 2-trifluoromethoxyphenyl, 2,6-dichlorophenyl, 2,6-diiodophenyl, unsubstituted or substituted guanidino- or amidino-phenyl, $$(CH_2)_2-NH\overset{NH}{\underset{}{\|}}NH_2, \quad (CH_2)_3-NH\overset{NH}{\underset{}{\|}}NH_2,$$

$$(CH_2)_3-\overset{NH}{\underset{NH_2}{\|}} \text{ or } (CH_2)_4-\overset{NH}{\underset{NH_2}{\|}};$$

and X is oxygen or sulfur.

3. A compound according to claim 2 wherein
$R_1$ and $R_2$ are each independently hydrogen, 7-methyl, 6- or 7-chloro, 7-nitro or 7-trifluoromethyl, or $R_1$ and $R_2$ together form 6,7-benzo;
n is 0;
$R_3$ is hydrogen or methyl; and
$R_4$ is 2-chlorophenyl, 2-bromophenyl, 2-iodophenyl, 2,6-dichlorophenyl, or 2-trifluoromethoxy.

4. A compound according to claim 2 selected from:

2) 2-(2-Chloro-phenylamino)-benzo[d][1,3]oxazin-4-one;
3) 2-(2-Bromo-phenylamino)-benzo[d][1,3]oxazin-4-one;
4) 2-(2-Iodo-phenylamino)-benzo[d][1,3]oxazin-4-one;
9) 2-(2-Trifluoromethoxy-phenylamino)-benzo[d][1,3] oxazin-4-one;
20) 2-(2-Iodo-phenylamino)-naphtho[2,3-d][1,3]oxazin-4-one;
28) 2-(2-Iodo-phenylamino)-7-methyl-benzo[d][1,3]-oxazin-4-one;
22) 6-Chloro-2-(2-iodo-phenylamino)-benzo[d][1,3]-oxazin-4-one;

23) 7-Chloro-2-(2-iodo-phenylamino)-benzo[d][1,3]oxazin-4-one;
29) 6,7-Dichloro-2-(2-iodo-phenylamino)-benzo[d][1,3]oxazin-4-one;
30) 2-(2-Iodo-phenylamino)-7-nitro-benzo[d][1,3]oxazin-4-one;
31) 2-(2-Iodo-phenylamino)-7-trifluoromethyl-benzo[d][1,3]oxazin-4-one;
45) 2-(2-Chloro-phenylamino)-7-methyl-benzo[d][1,3]oxazin-4-one;
46) 6,7-Difluoro-2-(2-iodo-phenylamino)benzo[d][1,3]oxazin-4-one;
47) 7-Fluoro-2-(2-iodo-phenylamino)-benzo[d][1,3]oxazin-4-one;
48) 6,7-Dichloro-2-(2-chloro-phenylamino)benzo[d][1,3]oxazin-4-one;
49) 2-(2-Iodo-phenylamino)-7-trifluoromethylbenzo[d][1,3]oxazin-4-one;
50) 7-Chloro-2-(2,6-dichloro-phenylamino)benzo[d][1,3]oxazin-4-one;
52) 2-(2-Chloro-phenylamino)-7-nitro-benzo[d][1,3]oxazin-4-one; and
53) 2-(2,6-Dichloro-phenylamino)-benzo[d][1,3]oxazin-4-one.

5. A compound according to claim 1 wherein $R_1$ and $R_2$ are each hydrogen, methyl, amidino, or guanidino;

n is 1;

$R_3$ is methyl or ethyl;

$R_4$ is phenyl, phenyl substituted by from 1 to 2 substituents selected from fluoro, chloro, bromo, iodo, alkyl, alkylthio, trifluoromethyl, amidino, guanidino, or $R_4$ is heteroaryl.

6. A compound according to claim 5 wherein $R_1$ and $R_2$ are each independently hydrogen, methyl, 6- or 7-amidino, or 6- or 7-guanidino;

n is 1;

$R_3$ is methyl or ethyl;

$R_4$ is phenyl, 2-iodophenyl, 2-bromophenyl, 2-thiomethylphenyl, 3-thienyl, and 2-trifluoromethylphenyl, 3-amidinophenyl, 4-amidinophenyl, 3-guanidinophenyl, 4-guanidinophenyl,

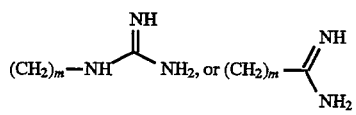

where m is an integer of from 2 to 5.

7. A compound according to claim 5 selected from:

12) 2-Iodo-N-methyl-N-(4-oxo-4H-benzo[d][1,3]oxazin-2-yl)-benzamide;
13) 2,6-Dichloro-N-methyl-N-(4-oxo-4H-benzo[d][1,3]oxazin-2-yl)-benzamide;
14) 2-Bromo-N-methyl-N-(4-oxo-4H-benzo[d][1,3]oxazin-2-yl)-benzamide;
15) N-Methyl-2-methylsulfanyl-N-(4-oxo-4H-benzo[d][1,3]oxazin-2-yl)-benzamide;
16) N-Methyl-N-(4-oxo-4H-benzo[d][1,3]oxazin-2-yl)-2-trifluoromethyl-benzamide;
17) N-Methyl-N-(4-oxo-4H-benzo[d][1,3]oxazin-2-yl)-benzamide;
18) N-Ethyl-2-iodo-N-(4-oxo-4H-benzo[d][1,3]oxazin-2-yl)-benzamide;
32) Thiophene-3-carboxylic acid methyl-(4-oxo-4H-benzo[d][1,3]oxazin-2-yl)-amide;
40) 2-Iodo-N-methyl-N-(6-methyl-4-oxo-4H-benzo[d][1,3]oxazin-2-yl)-benzamide;
55) 2-Iodo-N-methyl-N-(7-methyl-4-oxo-4H-benzo[d][1,3]oxazin-2-yl)-benzamide; and
56) N-(6,7-Dichloro-4-oxo-4H-benzo[d][1,3]oxazin-2-yl)-2-iodo-N-methyl-benzamide.

8. A pharmaceutical composition comprising a therapeutically effective amount of one or more compounds according to claim 1 and a pharmaceutically acceptable carrier in unit dosage form.

9. A method for treating a condition advantageously affected by the inhibition of serine proteases which comprises administering one or more compounds according to claim 1 to a patient in need of such treatment.

10. A method for treating inflammation which comprises administering one or more compounds according to claim 1 to a patient in need of such treatment.

11. A method for treating Alzheimer's disease which comprises administering one or more compounds according to claim 1 to a patient in need of such treatment.

12. A method for treating Alzheimer's disease which comprises administering one or more compounds of Formula II below to a patient in need of said treatment

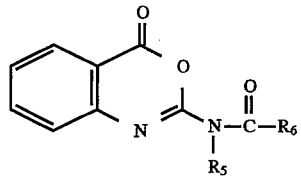

or a pharmaceutically acceptable salt thereof wherein $R_5$ is hydrogen, methyl, ethyl, or phenyl and $R_6$ is alkyl of from 1 to 10 carbons, alkenyl of from 2 to 10 carbons, cycloalkyl of from 3 to 6 carbons, or arylalkyl.

13. A method according to claim 11 which comprises administering one or more compounds selected from 64) Heptanoic acid methyl-(4-oxo-4H-benzo[d][1,3]oxazin-2-yl)-amide;
65) Cyclohexanecarboxylic acid methyl-(4-oxo-4H-benzo[d][1,3]oxazin-2-yl)-amide;
66) Heptanoic acid ethyl-(4-oxo-4H-benzo[d][1,3]oxazin-2-yl)-amide;
67) Undecanoic acid methyl-(4-oxo-4H-benzo[d][1,3]oxazin-2-yl)-amide;
68) N-Methyl-N-(4-oxo-4H-benzo[d][1,3]oxazin-2-yl)-3-phenyl-propionamide;
69) N-Methyl-N-(4-oxo-4H-benzo[d][1,3]oxazin-2-yl)-acetamide;
70) Hexanoic acid methyl-(4-oxo-4H-benzo[d][1,3]oxazin-2-yl)-amide;
71) Octanoic acid methyl-(4-oxo-4H-benzo[d][1,3]oxazin-2-yl)-amide;
72) N-Methyl-N-(4-oxo-4H-benzo[d][1,3]oxazin-2-yl)-propionamide;
73) Pentanoic acid methyl-(4-oxo-4H-benzo[d][1,3]oxazin-2-yl)-amide;
74) Heptanoic acid (4-oxo-4H-benzo[d][1,3]oxazin-2-yl)-amide;
75) Heptanoic acid (4-oxo-4H-benzo[d][1,3]oxazin-2-yl)-phenyl-amide; and
76) Hept-3-enoic acid methyl-(4-oxo-4H-benzo[d][1,3]oxazin-2-yl)-amide.

14. A compound according to claim 1 and selected from:

3-Guanidino-N-methyl-N-(4-oxo-4H-benzo[d][1,3]
oxazin-2-yl)-propionamide;

4-Guanidino-N-methyl-N-(4-oxo-4H-benzo[d][1,3]
oxazin-2-yl)-butyramide;

4-Carbamimidoyl-N-methyl-N-(4-oxo-4H-benzo[d][1,3]
oxazin-2-yl)-butyramide;

5-Carbamimidoyl-pentanoic acid methyl-(4-oxo-4H-
benzo[d][1,3]oxazin-2-yl)-amide;

3-Guanidino-N-methyl-N-(4-oxo-4H-benzo[d][1,3]
oxazin-2-yl)-propionamide;

4-Guanidino-N-methyl-N-(4-oxo-4H-benzo[d][1,3]
oxazin-2-yl)-butyramide;

4-Carbamimidoyl-N-methyl-N-(4-oxo-4H-benzo[d][1,3]
oxazin-2-yl)-butyramide; and

5-Carbamimidoyl-pentanoic acid methyl-(4-oxo-4H-
benzo[d][1,3]oxazin-2-yl)-amide.

15. A compound according to claim 1 and selected from:

N-(7-Guanidino-4-oxo-4H-benzo[d][1,3]oxazin-2-yl)-N-
methyl-benzamide;

N-(7-Carbamimidoyl-4-oxo-4H-benzo[d][1,3]oxazin-2-
yl)-N-methyl-benzamide;

N-(6-Guanidino-4-oxo-4H-benzo[d][1,3]oxazin-2-yl)-N-
methyl-benzamide;

N-(6-Carbamimidoyl-4-oxo-4H-benzo[d][1,3]oxazin-2-
yl)-N-methyl-benzamide;

N-(7-Guanidino-4-oxo-4H-benzo[d][1,3]thiazin-2-yl)-N-
methyl-benzamide;

N-(7-Carbamimidoyl-4-oxo-4H-benzo[d][1,3]thiazin-2-
yl)-N-methyl-benzamide;

N-(6-Guanidino-4-oxo-4H-benzo[d][1,3]thiazin-2-yl)-N-
methyl-benzamide; and

N-(6-Carbamimidoyl-4-oxo-4H-benzo[d][1,3]thiazin-2-
yl)-N-methyl-benzamide.

16. A compound according to claim 1 and selected from:

4-Guanidino-N-methyl-N-(4-oxo-4H-benzo[d][1,3]
oxazin-2-yl)-benzamide;

3-Guanidino-N-methyl-N-(4-oxo-4H-benzo[d][1,3]
oxazin-2-yl)-benzamide;

4-Carbamimidoyl-N-methyl-N-(4-oxo-4H-benzo[d][1,3]
oxazin-2-yl)-benzamide;

3-Carbamimidoyl-N-methyl-N-(4-oxo-4H-benzo[d][1,3]
oxazin-2-yl)-benzamide;

N-{4-[Methyl-(4-oxo-4H-benzo[d][1,3]oxazin-2-yl)-
amino]-phenyl}-guanidine;

N-{3-[Methyl-(4-oxo-4H-benzo[d][1,3]oxazin-2-yl)-
amino]-phenyl}-guanidine;

4-[Methyl-(4-oxo-4H-benzo[d][1,3]oxazin-2-yl)-amino]-
benzamide;

3-[Methyl-(4-oxo-4H-benzo[d][1,3]oxazin-2-yl)-amino]-
benzamide;

4-Carbamimidoyl-N-methyl-N-(4-oxo-4H-benzo[d][1,3]
thiazin-2-yl)-benzamide;

4-Guanidino-N-methyl-N-(4-oxo-4H-benzo[d][1,3]
thiazin-2-yl)-benzamide;

3-Carbamimidoyl-N-methyl-N-(4-oxo-4H-benzo[d][1,3]
thiazin-2-yl)-benzamide; and

3-Guanidino-N-methyl-N-(4-oxo-4H-benzo[d][1,3]
thiazin-2-yl)-benzamide.

17. A method of treating a condition advantageously affected by the inhibition of serine proteases which comprises administering one or more compounds of Formula III below to a patient in need of said treatments

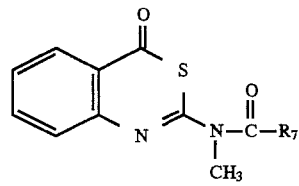

or a pharmaceutically acceptable salt thereof wherein
$R_7$ is

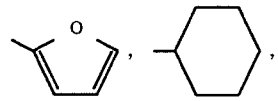

or $(CH_2)_5CH_3$.

$R_7$ is

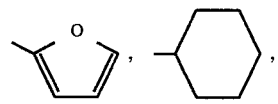

or $(CH_2)_5CH_3$.

18. A method according to claim 16 wherein the compound is selected from:

Furan-2-carboxylic acid methyl-(4-oxo-4H-benzo[d][1,3]
thiazin-2-yl)-amide;

Cyclohexanecarboxylic acid methyl-(4-oxo-4H-benzo[d]
[1,3]thiazin-2-yl)-amide; and Heptanoic acid methyl-(4-oxo-4H-benzo[d][1,3]thiazin-
2-yl)-amide.

19. A method of treating inflammation which comprises administering one or more compounds of Formula III below to a patient in need of said treatment

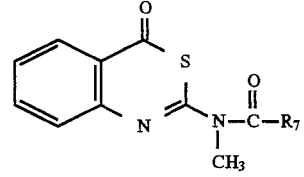

or a pharmaceutically acceptable salt thereof wherein
$R_7$ is

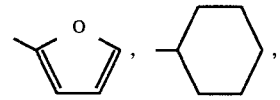

or $(CH_2)_5CH_3$.

20. A method according to claim 18 wherein the compound is selected from:

Furan-2-carboxylic acid methyl-(4-oxo-4H-benzo[d][1,3]
thiazin-2-yl)-amide;

Cyclohexanecarboxylic acid methyl-(4-oxo-4H-benzo[d]
[1,3]thiazin-2-yl)-amide; and Heptanoic acid methyl-(4-oxo-4H-benzo[d][1,3]thiazin-
2-yl)-amide.

* * * * *